United States Patent [19]
Coleman et al.

[11] 4,052,985
[45] Oct. 11, 1977

[54] APPARATUS FOR MEDICINALLY SPRAYING AN EYEBALL

[76] Inventors: D. Jackson Coleman, 223 Maple St., Haworth, N.J. 07641; Stephen L. Trokel, 1192 Park Ave., New York, N.Y. 10028

[21] Appl. No.: 700,481

[22] Filed: June 28, 1976

[51] Int. Cl.² .................................................. A61M 11/00
[52] U.S. Cl. .................................. 128/173 R; 128/249
[58] Field of Search ................... 128/233, 249, 173 R

[56] References Cited
U.S. PATENT DOCUMENTS

| | | | |
|---|---|---|---|
| 2,330,695 | 9/1943 | Eweson | 128/249 |
| 2,906,463 | 9/1959 | Curry | 128/173 R X |
| 3,107,670 | 10/1963 | Silson et al. | 128/173 R |
| 3,200,817 | 8/1965 | Brainard | 128/173 R |
| 3,522,806 | 8/1970 | Szekely | 128/173 R |
| 3,841,533 | 10/1974 | Carroll et al. | 128/173 R |

*Primary Examiner*—John D. Yasko
*Attorney, Agent, or Firm*—Kirschstein, Kirschstein, Ottinger & Frank

[57] ABSTRACT

An apparatus for administering a fine mist of an ophthalmic solution to the eyeball of a human. The apparatus is a spray applicator which features the provision of a baffle in the lower portion of an eyecup. The baffle is spaced from the inner surface of the eyecup, with the lateral ends or the entire lower periphery of the baffle being attached to the inner surface of the eyecup. A container such as an aerosol can or plastic squeeze bottle holding the ophthalmic solution is provided, together with ancillary elements to transmit the solution, so that the ophthalmic solution can be projected at will, i.e. when the eyecup is emplaced over an eyeball, into the lower portion of the eyecup opposite the baffle, so that the solution impinges on the baffle rather than directly impinging on the eyeball, the solution thus being effectively dispersed into a mist of small droplets within the eyecup, which mist thus uniformly and gently coats the outer surface of the eyeball. The central portion of the eyecup is preferably composed of a material such as glass, plexiglass or lucite which transmits light, i.e. the central portion of the eyecup is translucent or transparent.

15 Claims, 4 Drawing Figures

APPARATUS FOR MEDICINALLY SPRAYING AN EYEBALL

BACKGROUND OF THE INVENTION

1. Field of the Invention

The invention relates to ophthalmic spray applicators.

2. Description of the Prior Art

Various types of apparatus and devices have been suggested in the prior art for the administering of an ophthalmic solution to the eyeball. These prior art devices generally entail the direct injection of the solution into the eyecup, as a spray or mist which impinges directly on the eyeball. Among the many prior art references may be mentioned U.S. Pat. Nos. 1,437,435; 1,557,620; 2,328,627; 2,330,695; 2,482,431; 2,754,821; 3,170,462; 3,261,355; 3,279,466; 3,392,725 and 3,446,209.

SUMMARY OF THE INVENTION

1. Purposes of the Invention

It is an object of the present invention to provide an improved ophthalmic spray applicator.

Another object is to provide an applicator which dispenses ophthalmic solution to the eyeball of a human in the form of a fine mist which gently, effectively and uniformly coats the eyeball.

An additional object is to provide an applicator which prevents the direct dissemination of ophthalmic solution from a container holding such solution to an eyeball.

An additional object is to provide an applicator which induces the patient to keep the eye open and eyeball accessible, by providing an eyecup in the applicator which has a central portion which transmits light.

Still another object is to prevent injury to the eyeball when dispensing an ophthalmic solution.

Still a further object is to uniformly dispense and coat an ophthalmic solution onto the eyeball of a human.

An object is to prevent any plugs or particles of solid material which may deposit in the solution supply means of an applicator from reaching or contacting the eyeball.

These and other objects and advantages of the present invention will become evident from the description which follows.

2. Brief Description of the Invention

In the present invention, an improved spray applicator for the transmission of a coating of an ophthalmic solution uniformly onto the outer surface of a human eyeball is provided. The ophthalmic solution will generally be an aqueous isotonic solution containing dissolved ingredients which are beneficial to or have a salutary, antiseptic or salubrious effect on the tissues of the eyeball. Such ingredients typically include benzalkonium chloride, thimerosal, peppermint water, camphor water, sodium bisulfite, sodium chloride, sodium borate, boric acid, phenylephrine hydrochloride etc. The ophthalmic solution may also consist of a buffered aqueous saline solution employed merely to rinse particulate material such as dust or dirt from the eyeball, e.g. when a person has been working for some time in a dusty environment as in a factory, or when a person has been walking on a sandy beach or trash-filled city street on a windy day.

The improved ophthalmic spray applicator is provided with an eyecup which fits over the opened eye. The eyecup will usually be generally hemispherical in configuration, however the term hemispherical will be understood to encompass and include other similar eyecup configurations such as hemioval, conical etc. The eyecup is characterized by the provision of a baffle within its lower portion. The baffle of the present invention is spaced from the inner surface of the eyecup and is generally parallel to the inner surface of the eyecup, although the baffle may converge towards the inner surface of the eyecup in a downwards direction. The lateral ends of the baffle, or the entire lower periphery of the baffle, is attached to the inner surface of the eyecup, so that the baffle is an integral connected part of the eyecup. The assemblage is completed by the provision of suitable means to project an ophthalmic solution at will into a specific portion of the eyecup, namely the lower portion of the eyecup opposite the baffle, so that the solution impinges on the baffle rather than directly impinging on the eyeball, with the solution thus being effectively dispersed into a mist of small droplets within the eyecup, which mist gently, effectively and uniformly coats the outer surface of the eyeball.

The means to project the solution at will, i.e. when the eyecup is emplaced over an eyeball, will typically consist of an aerosol spray bottle or can, plastic squeeze bottle, any suitable container provided with a liquid pumping means e.g. a plunger cooperating with a piston within the container, etc., together with ancillary elements to transmit the stream of ophthalmic solution from the container holding a body of such solution to the eyecup. In most instances, the container will be a relatively small vessel integrally attached to the eyecup, so that the assemblage may be readily held in the hand of the user, who may be either the person whose eye is being treated, or a physician, a nurse, etc.

The device is further characterized in a preferred embodiment by the provision of a novel central portion of the eyecup, namely an eyecup central portion or region which transmits light. The central portion may be translucent or completely transparent, and is typically composed of glass, frosted glass, plexiglass, lucite or other plastic material which transmits light.

The baffle may either be a flat planar member, or curved; when the baffle is curved it will preferably have a radius of curvature which approximates the radius of curvature of the eyecup so that the baffle is uniformly parallel to the eyecup.

When the means to project the solution into the lower portion of the eyecup is an aerosol spray means, the provision of the baffle insures that the initial aerosol spray is further comminuted by contact with and impingement upon the baffle. When the means to project the solution into the lower portion of the eyecup is one of the devices mentioned, supra, which intermittently squirts or projects a spurt or linear stream of solution against the baffle, it has been found that the linear continuous or solid stream of solution is effectively converted into a dispersed mist of small droplets within the eyecup, which mist then disseminates onto the surface of the eyeball. In any event, the solution is preferably projected radially inwards into the lower portion of the eyecup and against the baffle, the solution being further comminuted by splashing or bouncing off the baffle and then impinging on the lower inner surface of the eyecup opposite to the baffle.

The ophthalmic spray applicator of the present invention presents several salient advantages. The ophthalmic or eye-washing solution is effectively dispersed into a fine mist within the eyecup per se, and prior to contacting the outer surface of the eyeball, so that the fine mist uniformly and gently coats the eyeball surface without pain or injury. Thus it is easier for the person being treated to accept the treatment and keep the eye open.

One of the major problems with eye droppers or devices which spray or squirt liquid directly into the eye is the great tendency for the eye almost automatically to close, in a sort of reflex action, to prevent the entry of the liquid. In such cases the liquid is dissipated onto the eyelid and does not penetrate into the eye, and proper and sufficient treatment is not attained.

The apparatus of the invention has wide utility. It has been estimated that 25 percent of the energy of an average person is expended, either directly or indirectly, through the eyes. Eyes can become irritated and red through hard usage and many feasible ophthalmic solutions may be used to alleviate these symptoms and improve the well-being of a person. As mentioned supra, the eyes of a person in certain occupations are constantly subjected to dust. Even persons in average occupations such as office work are subjected to the glare of lamps, close reading of printed numbers or words etc., all of which tires the eyes. Other factors which may require alleviation of tired eyes by means of an ophthalmic solution are smog and the glare of sunlight. The apparatus of the present invention helps to alleviate all the symptoms of tired eyes in an improved manner.

In addition, certain diseases of the eye are medicated by application to the eye of medicinal ophthalmic solutions of various types. Among these treatable eye diseases may be mentioned conjunctivitis or the so-called "pink eye", which spreads rapidly in urban areas, especially in the summertime, because urban mass transit necessitates that persons touch or hold surfaces such as railings or straps which have previously been touched or held by persons suffering from conjunctivitis. Thus, since most people habitually touch or rub their eyes from time to time, this contagious disease is rapidly spread and easily contracted. Another serious eye disease which is alleviated by an ophthalmic medicinal solution is glaucoma.

Another advantage is that if the present invention is used with an aerosol spray bottle, the baffle is needed to reduce the force of expelled vapor into the eye. With non-aerosol solution supply means, such as those mentioned supra, a mist, spurt or spray could also be expelled into the eye at too great a pressure without the baffle. In addition, with any type of solution supply means, the nozzle could clog due to evaporation of the liquid phase and deposition of solid salts or the like. Without the baffle, continued pressure would eventually dislodge the plug or clog, forcing the plug and medicine under pressure into the eye.

With regard to the provision of a central portion, section or region of the eyecup which transmits light, and which is either translucent or transparent, one prior art device has provided a red dot at this point for focusing of the eye. If this prior art device is used in a dark room such as a doctor's office, it is difficult to see the red dot and it is therefore hard to sight the device correctly. In the present invention, the user could focus on any light within the room and still use the device. The central light-transmitting section of the eyecup is used not for focusing the eye, but to have the user look at the light in order to keep the eye open.

The invention accordingly consists in the features of construction, combination of elements and arrangement of parts which will be exemplified in the device hereinafter described and of which the scope of application will be indicated in the appended claims.

BRIEF DESCRIPTION OF THE DRAWINGS

In the accompanying drawings in which are shown various possible embodiments of the invention.

DETAILED DESCRIPTION OF THE PREFERRED EMBODIMENTS

Figure 1:
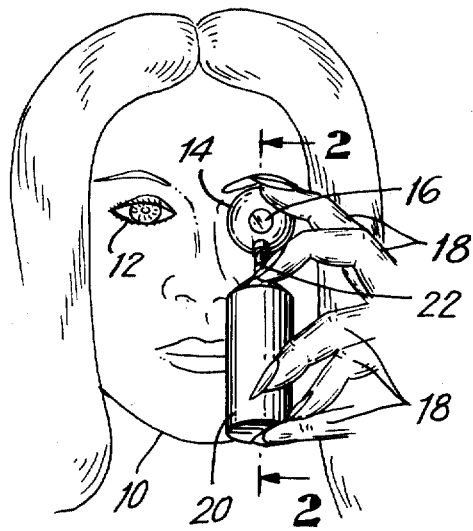
FIG. 1 is an elevation view of the present apparatus in usage, i.e. during application of an ophthalmic solution or the like to the eye of a human.

Referring now to FIG. 1, a head 10 of a human is shown, with the left eye, not shown, being subjected to treatment with the device of the present invention. A right eye 12 is shown in the open position, with the corresponding left eye also being open but covered by an eyecup 14. The eyecup 14 is provided with a central light-transmitting portion or region 16, which may be translucent or transparent and which is composed of any suitable material such as those mentioned supra. The eyecup 14 per se is composed of plastic, metal or the like, and is of generally hemispherical configuration as will appear infra. The device is held by fingers 18 of the hand of the user, who may be the person having the head 10, or a doctor or nurse or the like. A container 20 such as those mentioned supra holds a supply of ophthalmic solution, and a small duct or tube 22 extends from the container 20 to the eyecup 14 to transmit the solution to the eyecup.

Figure 2:
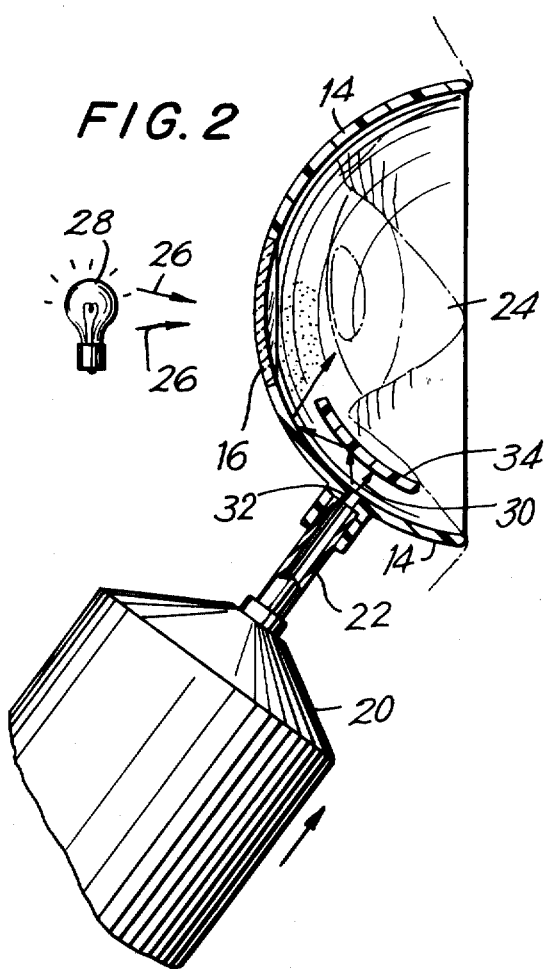
FIG. 2 is a sectional elevation view taken substantially along the lines 2—2 of FIG. 1.

FIG. 2 shows a left eye 24 of the head 10 in position and open within the eyecup 14. The eye 24 is staring through the central region 16 of eyecup 14 at light beams 26 emanating from a light source 28, which in this case is an electric light bulb. In accordance with the present invention, a stream 30 of ophthalmic solution is discharged from container 20 via tube 22 and through an opening 32 in the lower portion of eyecup 14. The solution stream 30 thus is projected against the outer surface of a baffle 34 provided within the lower portion of the eyecup 14. The baffle 34 in this embodiment is laterally attached at its lateral ends to the inner surface of the eyecup 14, and baffle 34 is spaced from the inner surface of eyecup 14 to allow for the comminuting of stream 30 into a plurality of small droplets, i.e. stream 30 is converted into a fine mist. As shown, the spacing of baffle 34 from eyecup 14 permits multiple amounts of comminution to take place as the liquid splashes off baffle 34 and contacts the inner surface of eyecup 14 between the eyecup 14 and baffle 34. Thus, the eventual comminution or shattering of stream 30 to a fine mist is enhanced by a multiple sequence and steps of alternate contact with baffle 34 and eyecup 14. The resulting fine mist moves upwards within eyecup 14 above baffle 34 and gently and uniformly coats the outer surface of the eye 24 with the ophthalmic solution 30.

In this preferred embodiment of the invention, the baffle 34 is curved and has a radius of curvature approximating that of the eyecup 14, so that baffle 34 is generally parallel to eyecup 14. In addition, the initial stream 30 is projected radially inwards against the baffle 34.

Figure 4:
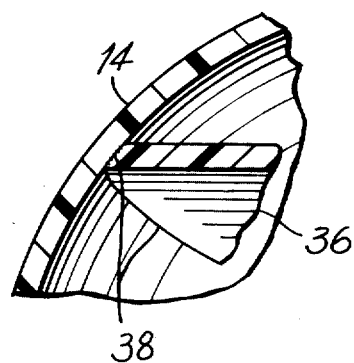
FIG. 4 is a sectional elevation view of a portion of the FIG. 3 embodiment of the invention, taken substantially along the lines 4—4 of FIG. 3.
Figure 3:
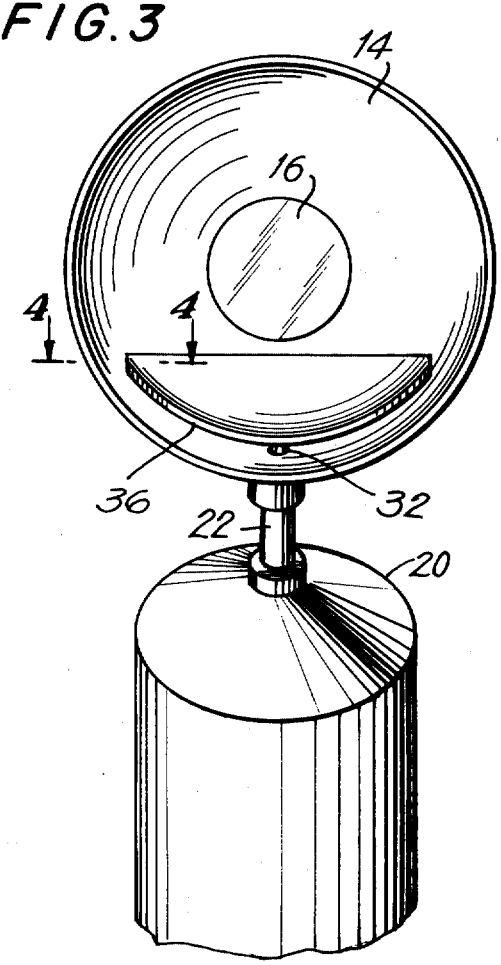
FIG. 3 is an elevation view of the internals of an alternative embodiment of the invention.

FIG. 3 illustrates an alternative embodiment of the invention in which the lower portion of a baffle 36 is arcuate, i.e. the baffle 36 is generally semi-circular and the entire lower periphery of baffle 36 is attached to the eyecup 14. FIG. 4 shows this arrangement in detail, i.e. the attachment 38 of the baffle 36 to the eyecup 14.

It thus will be seen that there is provided an ophthalmic spray applicator which achieves the various objects of the invention and which is well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art that although preferred and alternative embodiments have been shown and described in accordance with the Patent Statutes, the invention is not limited thereto or thereby.

Having thus described the invention, there is claimed as new and desired to be secured by Letters Patent:

1. An ophthalmic spray applicator which comprises a generally hemispherical eyecup, a baffle adjacent the annular periphery of said eyecup and within the lower portion of said eyecup, said baffle being generally parallel to and spaced from the inner surface of said eyecup with the lateral ends or entire lower periphery of said baffle being attached to the inner surface of said eyecup, means to project an ophthalmic solution into the lower portion of said eyecup opposite said baffle, so that said solution impinges on said baffle rather than directly impinging on an eyeball, said solution thereby being effectively dispersed into a mist of small droplets within said eyecup, and means in said eyecup to attract vision, said means to attract vision being rearward from both the annular periphery of said eyecup and said means to project an ophthalmic solution.

2. The applicator of claim 1 in which the baffle is curved.

3. The applicator of claim 2 in which the radius of curvature of the baffle approximates the radius of curvature of the eyecup.

4. The applicator of claim 1 in which the baffle is a flat planar member.

5. The applicator of claim 1 in which the means to project an ophthalmic solution into the lower portion of the eyecup is an aerosol spray means, whereby the initial aerosol spray is further comminuted by contact with the baffle.

6. The applicator of claim 1 in which the means to project an ophthalmic solution into the lower portion of the eyecup is a means to intermittently squirt a linear stream of solution against the baffle, so that the linear stream of solution is effectively converted into a dispersed mist of small droplets within the eyecup.

7. The applicator of claim 1 in which the ophthalmic solution is projected radially inwards into the lower portion of the eyecup and against the baffle.

8. The applicator of claim 1 in which the ophthalmic solution is an aqueous isotonic solution.

9. The applicator of claim 1 in which the means in said eyecup to attract vision is the central portion of the eyecup, and in which said central portion of the eyecup transmits light.

10. The applicator of claim 9 in which the central portion of the eyecup is translucent.

11. The applicator of claim 9 in which the central portion of the eyecup is transparent.

12. An ophthalmic spray applicator which comprises a generally hemispherical eyecup, the central portion of said eyecup being provided with means to attract vision, a baffle adjacent the annular periphery of said eyecup and within the lower portion of said eyecup, said baffle being generally parallel to and spaced from the inner surface of said eyecup with the lateral ends or entire lower periphery of said baffle being attached to the inner surface of said eyecup, and means to project an ophthalmic solution into the lower portion of said eyecup opposite said baffle, so that said solution impinges on said baffle rather than directly impinging on an eyeball, said solution thereby being effectively dispersed into a mist of small droplets within said eyecup.

13. The applicator of claim 12 in which the central portion of the eyecup is translucent.

14. The applicator of claim 12 in which the central portion of the eyecup is transparent.

15. The applicator of claim 12 in which the central portion of the eyecup is light transmissible, so that the central portion of the eyecup attracts vision when the eyecup is emplaced in juxtaposition with an open eye, with said open eye being covered by the eyecup.

* * * * *